(12) United States Patent
Predki et al.

(10) Patent No.: US 12,338,470 B2
(45) Date of Patent: Jun. 24, 2025

(54) ENZYMES AND SYSTEMS FOR SYNTHESIZING DNA

(71) Applicant: IRIDIA, INC., Carlsbad, CA (US)

(72) Inventors: Paul F. Predki, Carlsbad, CA (US); Stefen Boehme, Encinitas, CA (US)

(73) Assignee: IRIDIA, INC., Carlsbad, CA (US)

( * ) Notice: Subject to any disclaimer, the term of this patent is extended or adjusted under 35 U.S.C. 154(b) by 79 days.

(21) Appl. No.: 18/298,995

(22) Filed: Apr. 11, 2023

(65) Prior Publication Data

US 2024/0084284 A1   Mar. 14, 2024

Related U.S. Application Data

(62) Division of application No. 16/866,439, filed on May 4, 2020, now Pat. No. 11,655,465.

(60) Provisional application No. 62/842,333, filed on May 2, 2019.

(51) Int. Cl.
| | |
|---|---|
| *C12N 9/90* | (2006.01) |
| *B01L 3/00* | (2006.01) |
| *C12N 15/74* | (2006.01) |
| *C12P 19/34* | (2006.01) |

(52) U.S. Cl.
CPC ............... *C12N 9/90* (2013.01); *B01L 3/508* (2013.01); *C12N 15/74* (2013.01); *C12P 19/34* (2013.01); *C12Y 599/01002* (2013.01); *B01L 2300/047* (2013.01)

(58) Field of Classification Search
CPC ........... C12N 9/90; C12N 15/74; C12P 19/34; C12Y 599/01002
See application file for complete search history.

(56) References Cited

U.S. PATENT DOCUMENTS

| | | | |
|---|---|---|---|
| 8,153,590 | B2 | 4/2012 | Lu et al. |
| 8,202,689 | B2 | 6/2012 | Heller et al. |
| 8,283,165 | B2 | 10/2012 | Hogan et al. |
| 8,512,947 | B2 | 8/2013 | Mutharasan et al. |
| 9,322,820 | B2 | 4/2016 | Blick et al. |
| 9,488,600 | B2 | 11/2016 | Blick et al. |
| 9,551,697 | B2 | 1/2017 | Chen |
| 10,196,680 | B2 | 2/2019 | Sharaf et al. |
| 10,438,662 | B2 | 10/2019 | Predki |
| 10,443,096 | B2 | 10/2019 | Ju et al. |
| 10,640,822 | B2 | 5/2020 | Predki et al. |
| 10,714,178 | B2 | 7/2020 | Predki et al. |
| 10,859,562 | B2 | 12/2020 | Predki et al. |
| 10,995,373 | B2 | 5/2021 | Predki et al. |
| 11,505,825 | B2 | 11/2022 | Predki |
| 11,655,465 | B1 | 5/2023 | Predki et al. |
| 2001/0026918 | A1 | 10/2001 | Collins et al. |
| 2005/0053968 | A1 | 3/2005 | Bharadwaj et al. |
| 2009/0098119 | A1 | 4/2009 | Lu et al. |
| 2009/0203000 | A1 | 8/2009 | Mutharasan et al. |
| 2009/0221443 | A1 | 9/2009 | Heller et al. |
| 2012/0058468 | A1 | 3/2012 | McKeown |
| 2012/0322109 | A1 | 12/2012 | Shuman et al. |
| 2012/0326732 | A1 | 12/2012 | Cho et al. |
| 2013/0264207 | A1 | 10/2013 | Ju et al. |
| 2014/0266147 | A1 | 9/2014 | Blick et al. |
| 2015/0107996 | A1 | 4/2015 | Chen |
| 2016/0025655 | A1 | 1/2016 | Blick et al. |
| 2016/0223538 | A1 | 8/2016 | Mcalpine et al. |
| 2017/0275678 | A1 | 9/2017 | Sharaf et al. |
| 2019/0080760 | A1 | 3/2019 | Predki et al. |
| 2019/0136307 | A1 | 5/2019 | Predki et al. |
| 2019/0341108 | A1 | 11/2019 | Predki et al. |
| 2019/0383788 | A1 | 12/2019 | Predki et al. |
| 2020/0224264 | A1 | 7/2020 | Predki et al. |

FOREIGN PATENT DOCUMENTS

| | | |
|---|---|---|
| WO | WO 2017/151680 | 9/2017 |
| WO | WO 2018/081745 | 5/2018 |
| WO | WO 2019/213437 | 11/2019 |
| WO | WO-2020/051501 A1 | 3/2020 |

OTHER PUBLICATIONS

Benner S., et al., "Sequence-specific detection of individual DNA polymerase complexes in real time using a nanopore," Nature Nanotechnology, 2007, 2(11):718-724.

International Search Report of International Application No. PCT/US2017/020044, prepared by the International Searching Authority, date mailed: Aug. 16, 2017, 4 pages.

International Search Report of International Application No. PCT/US2017/059100, prepared by the International Searching Authority, date mailed: Jan. 18, 2018, 3 pages.

International Search Report of International Application No. PCT/US2019/030463, prepared by the International Searching Authority, date mailed: Aug. 30, 2019, 5 pages.

Manrao E., et al., "Reading DNA at single-nucleotide resolution with a mutant MspA nanopore and phi29 DNA polymerase," Nature Biotechnology, 2012, 30(4):349-354.

Minkah N., et al., "Variola Virus Topoisomerase: DNA Cleavage Specificity and Distribution of Sites in Poxvirus Genomes," Virology, 2007, 365(1):60-69.

Palaniyar N., et al., "SFV topoisomerase: sequence specificity in a genetically mapped interval," Virology, 1996, 221(2):351-4.

(Continued)

*Primary Examiner* — Iqbal H Chowdhury
(74) *Attorney, Agent, or Firm* — Hoxie & Associates LLC

(57) ABSTRACT

The disclosure provides novel topoisomerases which exhibit weakened ability to form a covalent bond to the 5'-(C/T)CCTT-3'recognition site in the presence of increased NaCl concentrations relative to wild-type, together with novel methods for synthesizing DNA in the 3' to 5' direction using the novel topoisomerase; and other compounds, compositions, methods and devices comprising or utilizing topoisomerases which exhibit reduced covalent bond formation to the 5'-(C/T)CCTT-3' recognition site in the presence of increased NaCl concentrations, relative to wild-type.

5 Claims, 4 Drawing Sheets
Specification includes a Sequence Listing.

(56) References Cited

OTHER PUBLICATIONS

Reed et al., "Characterization of DNA Binding by the Isolated N-Terminal Domain of Vaccinia Virus DNA Topoisomerase IB," Biochemistry, 2017, 56:3307-3317.

Shuman S., "Novel Approach to Molecular Cloning and Polynucleotide Synthesis Using Vaccinia DNA Topoisomerase*," J Biol Chem., 1994, 269(51):32678-84.

Shuman S., "Vaccinia virus DNA topoisomerase: a model eukaryotic type IB enzyme," Biochimica et Biophysica Acta, 1998, 1400:321-337.

Stivers J.T., et al., "Vaccinia DNA Topoisomerase I: Single-Turnover and Steady-State Kinetic Analysis of the DNA Strand Cleavage and Ligation Reactions," Biochemistry, 1994, 33(1):327-339.

Tian et al., "Individual Nucleotide Bases, Not Base Pairs, Are Critical for Triggering Site-specific DNA Cleavage by Vaccinia Topoisomerase," The Journal of Biological Chemistry, 2004, 279(38):39718-39726.

SEQUENCE LISTING

```
Sequence total quantity: 10
SEQ ID NO: 1                moltype = AA   length = 314
FEATURE                     Location/Qualifiers
REGION                      1..314
                            note = Wild-Type Protein
source                      1..314
                            mol_type = protein
                            organism = synthetic construct
SEQUENCE: 1
MRALFYKDGK LFTDNNFLNP VSDDNPAYEV LQHVKIPTHL TDVVVYEQTW EEALTRLIFV    60
GSDSKGRRQY FYGKMHVQNR NAKRDRIFVR VYNVMKRINC FINKNIKKSS TDSNYQLAVF   120
MLMETMFFIR FGKMKYLKEN ETVGLLTLKN KHIEISPDEI VIKFVGKDKV SHEFVVHKSN   180
RLYKPLLKLT DDSSPEEFLF NKLSERKVYE CIKQFGIRIK DLRTYGVNYT FLYNFWTNVK   240
SISPLPSPKK LIALTIKQTA EVVGHTPSIS KRAYMATTIL EMVKDKNFLD VVSKTTFDEF   300
LSIVVDHVKS STDG                                                    314

SEQ ID NO: 2                moltype = DNA   length = 942
FEATURE                     Location/Qualifiers
misc_feature                1..942
                            note = Wild-Type DNA
source                      1..942
                            mol_type = other DNA
                            organism = synthetic construct
SEQUENCE: 2
atgcgtgcac ttttttataa agatggtaaa ctcttttaccg ataataattt tttaaatcct    60
gtatcagacg ataatccagc gtatgaggtt ttgcaacatg ttaaaattcc tactcattta   120
acagatgtag tagtatatga acaaacgtgg gaagaggcat taactagatt aatttttgtg   180
ggaagcgatt caaaaggacg tagacaatac ttttacggca aaatgcatgt acagaatcgc   240
aacgctaaaa gagatcgtat ttttgttaga gtatataacg ttatgaaacg aattaattgt   300
tttataaaca aaaatataaa gaaatcgtcc acagattcca attatcagtt ggcggttttt   360
atgttaatgg aaactatgtt ttttattaga tttggtaaaa tgaatatctt aaggagaat   420
gaaacagtag ggttattaac actaaaaaat aaacacataa aataagtcc cgatgaaata   480
gttatcaagt ttgtaggaaa ggacaaagtt tcacatgaat tgttgttca taagtctaat   540
agactatata aaccgctatt gaactgacg gatgattcta gtcccgaaga atttctgttc   600
aacaaactaa gtgaacgaaa ggtatacgaa tgtatcaaac agtttggtat tagaatcaag   660
gatctccgaa cgtatggagt caattatacg ttttttatata atttttggac aaatgtaaag   720
tccatatctc ctcttccgtc accaaaaaag ttaatagcgt taactatcaa acaaactgct   780
gaagtggtag gtcatactcc atcaatttca aaaagagctt acatggcaac gactattta   840
gaaatggtaa aggataaaaa tttttagat gtagtatcta aaactacgtt cgatgaattc   900
ctatctatag tcgtagatca cgttaaatca tctacgatg ga                      942

SEQ ID NO: 3                moltype = AA   length = 313
FEATURE                     Location/Qualifiers
REGION                      1..313
                            note = Wild-Type Protein
SITE                        66
                            note = Xaa can be any naturally occurring amino acid
REGION                      68..69
                            note = Xaa can be any naturally occurring amino acid
SITE                        79
                            note = Xaa can be any naturally occurring amino acid
source                      1..313
                            mol_type = protein
                            organism = synthetic construct
SEQUENCE: 3
RALFYKDGKL FTDNNFLNPV SDDNPAYEVL QHVKIPTHLT DVVVYEQTWE EALTRLIFVG    60
SDSKGXRXXF YGKMHVQNXN AKRDRIFVRV YNVMKRINCF INKNIKKSST DSNYQLAVFM   120
LMETMFFIRF GKMKYLKENE TVGLLTLKNK HIEISPDEIV IKFVGKDKVS HEFVVHKSNR   180
LYKPLLKLTD DSSPEEFLFN KLSERKVYEC IKQFGIRIKD LRTYGVNYTF LYNFWTNVKS   240
ISPLPSPKKL IALTIKQTAE VVGHTPSISK RAYMATTILE MVKDKNFLDV VSKTTFDEFL   300
SIVVDHVKSS TDG                                                     313

SEQ ID NO: 4                moltype = AA   length = 340
FEATURE                     Location/Qualifiers
REGION                      1..340
                            note = Mutant Protein
source                      1..340
                            mol_type = protein
                            organism = synthetic construct
SEQUENCE: 4
MKHHHHHHGG GSGDYKDDDD KGGGGSGRAL FYKDGKLFTD NNFLNPVSDD NPAYEVLQHV    60
KIPTHLTDVV VYEQTWEEAL TRLIFVGSDS KGRRAYFYGK MHVQNANAKR DRIFVRVYNV   120
MKRINCFINK NIKKSSTDSN YQLAVFMLME TMFFIRFGKM KYLKENETVG LLTLKNKHIE   180
ISPDEIVIKF VGKDKVSHEF VVHKSNRLYK PLLKLTDDSS PEEFLFNKLS ERKVYECIKQ   240
FGIRIKDLRT YGVNYTFLYN FWTNVKSISP LPSPKKLIAL TIKQTAEVVG HTPSISKRAY   300
MATTILEMVK DKNFLDVVSK TTFDEFLSIV VDHVKSSTDG                         340

SEQ ID NO: 5                moltype = DNA   length = 1020
```

```
FEATURE               Location/Qualifiers
misc_feature          1..1020
                      note = Mutant DNA
source                1..1020
                      mol_type = other DNA
                      organism = synthetic construct
SEQUENCE: 5
atgaaacacc atcatcacca tcacggcggc ggctctggcg attacaaaga cgatgacgac    60
aagggtggtg gcggctccgg tcgcgcgctg ttctataagg atggtaaact gtttaccgac   120
aacaatttcc tgaacccggt gagcgacgat aatccggcgt acgaagtgct gcaacacgtg   180
aaaattccga cgcacctgac cgacgttgtt gtgtacgagc aaacctggga agaagcgctg   240
acgcgcctga ttttgtcgg tagcgacagc aagggtcgtc gtgcatactt ttatggtaaa    300
atgcacgttc agaatgcgaa cgcaaagcgt gatcgtatct tcgtccgtgt gtataatgtt   360
atgaagcgca ttaattgttt catcaacaag aacatcaaga aagctcgac ggatagcaat     420
taccagctgg ccgtgttcat gttgatggaa accatgttct ttattcgttt cggtaagatg   480
aaatacctga agaaaacga aaccgtcggt ctgttgacgc tgaagaataa gcatatcgag    540
atcagcccgg atgaaattgt tatcaagttc gttggcaaag acaaagtttc ccacgaattc   600
gtcgtccaca agagcaatcg tctgtacaag ccgctgctga agttgaccga cgacagcagc   660
ccagaagaat ttctgtttaa caaactgagc gagcgtaaag tgtatgagtg cattaagcaa   720
tttggcattc gcatcaaaga tttgcgtacc tacggtgtca actacacttt cctctataac   780
ttctggacta acgttaaatc tattagcccg ctgccgagcc ctaaaaagtt aatcgccctg   840
accatcaaac agaccgctga agttgtgggc cacacgccct ctattagcaa gcgtgcatat   900
atggcgacca cgatcctgga aatggttaaa gataagaatt ttctggacgt cgttagcaaa   960
accacgtttg atgagttcct gagcattgtc gtggaccatg tgaaatccag caccgatggt  1020

SEQ ID NO: 6         moltype = DNA   length = 30
FEATURE              Location/Qualifiers
misc_feature         1..30
                     note = Donor Oligonucleotide
misc_difference      8..19
                     note = n is a, c, g, t, or absent
misc_difference      26..30
                     note = n is a, c, g, t, or absent
source               1..30
                     mol_type = other DNA
                     organism = synthetic construct
SEQUENCE: 6
cgaagggnnn nnnnnnnng tcgacnnnnn                                      30

SEQ ID NO: 7         moltype = DNA   length = 23
FEATURE              Location/Qualifiers
misc_feature         1..23
                     note = Topoisomerase Charged Oligonucleotides
source               1..23
                     mol_type = other DNA
                     organism = synthetic construct
SEQUENCE: 7
cacgtcaggc gtatccatcc ctt                                            23

SEQ ID NO: 8         moltype = DNA   length = 25
FEATURE              Location/Qualifiers
misc_feature         1..25
                     note = Topoisomerase Ligation Site
misc_difference      8..19
                     note = n is a, c, g, t, or absent
misc_feature         8..19
                     note = n (located from base position 8 to 19) refers to
                            Informational Sequence A or B, which can be from 3 to 12
                            nucleotides
source               1..25
                     mol_type = other DNA
                     organism = synthetic construct
SEQUENCE: 8
cgaagggnnn nnnnnnnng tcgac                                           25

SEQ ID NO: 9         moltype = DNA   length = 18
FEATURE              Location/Qualifiers
misc_feature         1..18
                     note = Topoisomerase Ligation Site
source               1..18
                     mol_type = other DNA
                     organism = synthetic construct
SEQUENCE: 9
cggccgtgtc gcccttcg                                                  18

SEQ ID NO: 10        moltype = DNA   length = 25
FEATURE              Location/Qualifiers
misc_feature         1..25
                     note = Ligated sequence
```

```
misc_difference    21..25
                   note = n is a, c, g, or t
source             1..25
                   mol_type = other DNA
                   organism = synthetic construct
SEQUENCE: 10
cggccgtgtc gcccttcggc nnnnn                                         25
```

ENZYMES AND SYSTEMS FOR SYNTHESIZING DNA

CROSS-REFERENCE TO RELATED APPLICATIONS

This application is a divisional application of U.S. patent application Ser. No. 16/866,439 filed on May 4, 2020, which claims priority to, and the benefit of, U.S. Provisional Application No. 62/842,333, filed on May 2, 2019, the contents of each of which are incorporated herein by reference in their entireties.

FIELD

This invention relates to novel methods, compositions and nanopore devices to synthesize DNA, including novel topoisomerase enzymes, genes encoding them, and methods of making them.

BACKGROUND

Vaccinia topoisomerase is a type I DNA topoisomerase having the ability to cut DNA strands 3' of its recognition sequence of 5'-(C/T)CCTT-3', e.g., 5'-CCCTT-3', and to ligate, or rejoin the DNA back together again.

WO 2017/151680, published Sep. 8, 2017, WO 2018/081745, published May 3, 2018, and U.S. application Ser. No. 15/969745, filed May 2, 2018, US Publication US20190383788A1, published Dec. 19, 2019 and WO2020051501A1, published Mar. 12, 2020, the entire contents of which applications are incorporated herein by reference, are related applications describing, among other things, novel methods of synthesizing DNA using size exclusion chemistry. In particular embodiments, these applications describe the use of vaccinia topoisomerase to add nucleotides to a DNA strand in a controlled manner, using a nanopore-based device, wherein the DNA is moved in and out of reaction chambers through a nanopore which excludes passage of the larger enzymes, thus permitting controlled addition of nucleotides to build a strand having a desired sequence.

There is a need for optimized forms of topoisomerase enzymes for use in DNA synthesis, e.g., using nanopore devices as disclosed in the above-mentioned applications.

SUMMARY

As noted above, vaccinia topoisomerase is a type I DNA topoisomerase has the ability to cut DNA strands 3' of its recognition sequence of 5'-(C/T)CCTT-3', e.g., 5' CCCTT 3', and to ligate, or rejoin the DNA back together again. In some embodiments, oligonucleotide cassettes may be linked together by vaccinia topoisomerase to encode digital information. In such a case, each cassette contains the recognition sequence, thereby allowing it to be "charged" with topoisomerase, i.e., the plus strand of DNA is cleaved by the enzyme, and becomes transiently covalently bound to the DNA cassette. When an appropriate DNA acceptor is found, designated by 4 base pair overhang, the topoisomerase ligates the cassette to the DNA acceptor strand in a process called "bit addition" or "topogation". After ligating the DNA cassette onto a DNA acceptor strand, the topoisomerase is no longer bound to the DNA, and it is free to cleave DNA at another recognition sequence.

One potential drawback of this approach is that already-synthesized synthetic DNA chains may become scrambled by unchecked topoisomerase activity. To mitigate this potentially deleterious effect, we have isolated mutants of vaccinia topoisomerase that have a reduced ability to form covalent bonds to the 5'-(C/T)CCTT-3', e.g., 5'-CCCTT-3' recognition site in the presence of increased NaCl concentrations. Without being bound by theory, it appears that the salt sensitive topoisomerases described herein are less able to recognize the terminal 5'-(C/T)CCTT-3' region, so as to form a covalent bond with the 3'-phosphate on the terminal "T" nucleotide. Thus, the mutants allow for topogation, but not charging, at increased amounts of NaCl. Consequently, the charging can be carried out in a low salt medium, then the charged oligomers can be ligated ("topogated") to an acceptor DNA in medium having a higher salt concentration, In a particular embodiment, the mutant is the Q69A/R80A vaccinia topoisomerase double mutant.

The invention this provides in one embodiment, mutants of vaccinia topoisomerase that have weakened covalent binding to the 5'-(C/T)CCTT-3', e.g., 5'-CCCTT-3' recognition site in the presence of increased NaCl concentrations (M-Topoisomerase). Thus, the M-Topoisomerase allow for topogation, but not charging, at increased amounts of NaCl. In a particular embodiment, the M-Topoisomerase is the Q69A/R80A vaccinia topoisomerase double mutant.

In a further embodiment, the invention provides optimized genes encoding such M-Topoisomerase, and methods of making such mutant topoisomerase.

In a further embodiment, the invention provides a method for synthesizing DNA by size exclusion chemistry in a nanopore-based device, by ligation mediated by the M-Topoisomerase, e.g., in a nanopore-based device comprising one or more addition chambers or channels containing buffer solution and reagents for addition of one or more nucleotides or oligonucleotides to the DNA in blocked form, such that only a single nucleotide or oligonucleotide can be added in one reaction cycle; and one or more deblocking chambers or channels containing buffer solution and reagents for removing the blocker group from the DNA, wherein the addition chambers or channels are separated from the deblocking chambers or channels by one or more membranes comprising one or more nanopores, and wherein the DNA can pass through a nanopore and at least one of the reagents for addition of one or more nucleotides or oligonucleotides cannot, the method comprising moving the first end of a DNA strand having a first end and a second end, by electrical attraction, into an addition chamber or channel, whereby nucleotides or oligonucleotides are added to said first end in blocked form, using a charged M-Topoisomerase, moving the first end of the DNA with the added one or more nucleotides or oligonucleotides in blocked form into a deblocker chamber or channel, whereby the blocking group is removed from the added one or more nucleotides or oligonucleotides, and repeating steps a) and b), wherein the nucleotides or oligonucleotides added in step a) are the same or different, until the desired polymer sequence is obtained, for example wherein the second end of the polymer is bound to a surface, and/or for example, wherein the device comprises one or more first addition chambers or channels containing reagents suitable for adding a first type of monomer or oligomer and one or more second addition chambers containing reagents suitable for adding a second type of monomer or oligomer, and wherein in step a), the first end of the charged polymer is moved into either the first addition chamber or the second addition chamber, depending on whether it is desired to add a first type of monomer or oligomer or a second type of monomer or oligomer.

In a further embodiment, the invention provides a nanopore-based chip comprising a M-Topoisomerase.

In a further embodiment, the invention provides a DNA vector, wherein the vector is in linear form and comprises a M-Topoisomerase covalently bound to the 3'phosphate at each end, and also provides a method of inserting a DNA sequence into the vector, wherein the DNA sequence has compatible ends so the DNA sequence is ligated into the vector and the topoisomerase is released.

Further aspects and areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF DRAWINGS

The present invention will become more fully understood from the detailed description and the accompanying drawings, wherein.

DETAILED DESCRIPTION

Figure 1:
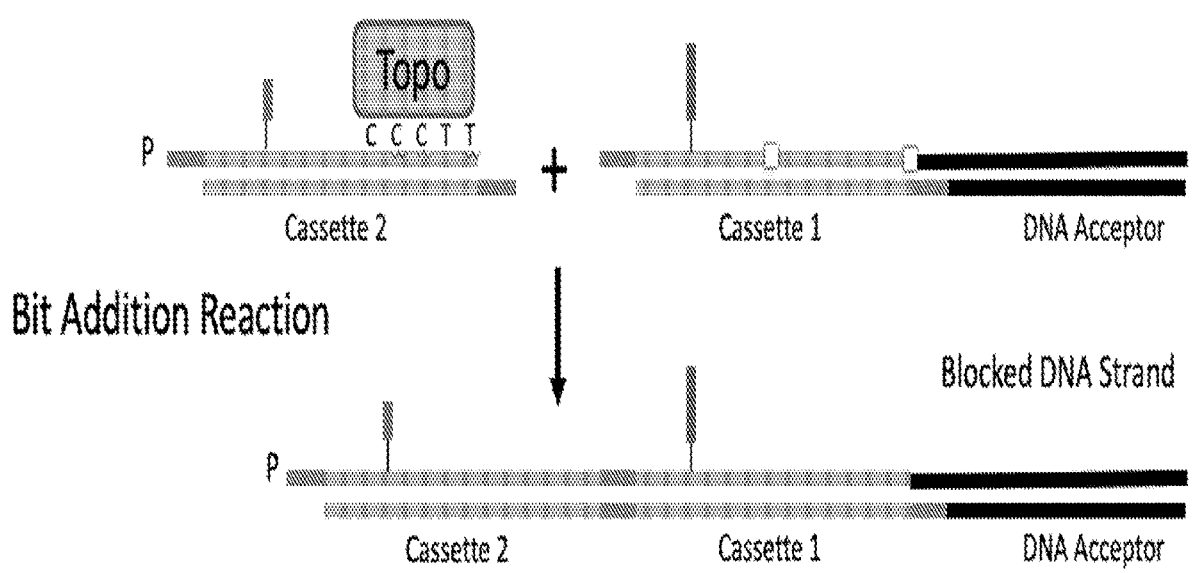
FIG. 1 schematically depicts "bit addition" or "topogation".

Blocks of (double stranded) nucleotides can be added to a strand of DNA, using site-specific recombinases, i.e., enzymes that spontaneously recognize and cleave at least one strand of a double strand of nucleic acids within a sequence segment known as the site-specific recombination sequence. Vaccinia virus topoisomerase I specifically recognizes DNA sequence 5'-(C/T)CCTT-3'. The topoisomerase binds to double-stranded DNA and cleaves it at the 5'-(C/T)CCTT-3' cleavage site. Note that the cleavage is not complete, as the topoisomerase only cleaves the DNA on one strand (although having a nearby nick on the other strand does cause a double-strand break of sorts), and when it cleaves, the topoisomerase attaches covalently to the 3' phosphate of the 3' nucleotide. The enzyme then remains covalently bound to the 3' end of the DNA, and can either religate the covalently held strand at the same bond as originally cleaved (as occurs during DNA relaxation), or it can religate to a heterologous acceptor DNA having compatible overhangs, creating a recombinant molecule. We create dsDNA donor oligonucleotides (e.g., comprising one of at least two different sequences, one for '0' and the other for '1') flanked by a topoisomerase recombination site and a restriction site that generates a topoisomerase ligation site.

The cassettes are Topo-charged; that is, they are covalently bound to a topoisomerase, which will bind them to a topoisomerase ligation site on the receiver oligonucleotide. When the growing DNA chain of the receiver is cleaved with a restriction enzyme it becomes capable of ligation to a Topo-charged cassette, or when the phosphatase removes the protecting 5' phosphate, it becomes capable of ligation to a Topo-charged cassette. So, one just needs to cycle the growing DNA from restriction enzyme to Topo-charged cassette successively, with each cycle adding another donor oligonucleotide.

In one embodiment, a phosphatase is used in combination with a restriction enzyme, or alternatively, a restriction digestion step to create a compatible overhang is omitted, in favor of using a 5' phosphate as blocking group and DNA phosphatase as a deblocking enzyme, or an overhang can be built into the sequence, e.g., using a DNA sequence:

```
                                                   (SEQ ID NO: 9)
    5' pCGGCCGTGTCGCCCTTCG

GCACAGCGGGAAGCCGp which when topo (*) charged gives:
    5' pCGGCCGTGTCGCCCTT*

GCACAGCGGGAAGCCGp
```

(wherein * indicates the topoisomerase and p indicates a terminal phosphate), which can then topogate to

```
    5' CGGCNNNNN

NNNNN
    wherein NNNN indicates any nucleotide sequence,
    to make
                                                  (SEQ ID NO: 10)
    5' pCGGCCGTGTCGCCCTTCGGCNNNNN

GCACAGCGGGAAGCCGNNNNN
``` which process can be repeated until the desired sequence is obtained. The sequence in bold can be varied to represent different bits, or to have bits 'attached' to it.

Single bases can be added using a similar strategy. In the presence of a suitable single stranded 'deprotected' 'acceptor' DNA, the topo-charged DNA is enzymatically and covalently ligated ('added') to the acceptor by the topoisomerase, which in the process becomes removed from the DNA. A type IIS restriction enzyme can then cleave all of the added DNA with the exception of a single base (the base which is being 'added'). The IIS site cleavage creates a ssDNA with a 5' phosphate. A DNA phosphatase is used to remove that too as part of the deprotection step. This process of deprotect-add can be repeated to add additional bases (bits). We have shown that it is feasible to use a Topo/TypeIIS restriction enzyme combination to add a single nucleotide to the 5' end of a target single stranded DNA. The use of a TypeIIS restriction enzyme enables cleavage of DNA in a location different from that of the recognition sequence. The use of inosines (which act as 'universal bases' and pair with any other base) in this system allows this reaction to occur without any specific sequence requirements in the target DNA. The identity of the nucleotide added to the single strand target DNA is the 3' nucleotide to which vaccinia topoisomerase conjugates via the 3' phosphate. Since the recognition sequence of vaccinia topoisomerase is (C/T)CCTT, we have used this system to add a 'T' to the target DNA. There is a related topoisomerase, SVF, that can use the recognition sequence CCCTG. Thus SVF can be used to add a 'G' instead of a 'T'. Paired with vaccinia topo, binary data can be encoded in T's and G's. As well, we have demonstrated conditions under which topoisomerase can be charged with CCCTG, CCCT and CCCTA.

In another approach to single base addition, a 5'phosphate provides a blocking group to provide single base addition in the 3' to 5' direction. The charging reaction charges the topoisomerase with a single T (or G, or other nucleotide as desired), having a 5' phosphate group. When the charged topoisomerase 'sees' a free 5' unblocked (unphosphorylated) single stranded DNA chain it will add the T to that chain, providing a DNA with a T added to the 5'. This addition is facilitated by the presence of an adapter DNA having sequences to which the topoisomerase and the single stranded acceptor DNA can bind. (Note that the adapter DNA is catalytic—it can be reused as a template in repeated reactions.) The added nucleotide has a 5' phosphate on it, so it won't be a substrate for further addition until it is exposed to a phosphatase, which removes the 5' phosphate. The process is repeated, using vaccinia topoisomerase to add a single "T" to the 5' end of a target single stranded DNA and SVF topoisomerase to add a single 'G', thus allowing construction of a sequence encoding binary information with T and G.

When the topoisomerase is charged, there is a mix of charged and uncharged product, which represents an equilibrium between the two species. The 'overhang' that the topoisomerase leaves can be designed in many ways, to optimize the efficiency of the reaction. Overhangs that are rich in GC tend to have faster charging reactions, but have charging equilibriums that tend to generate lower yield of product. We have found that having some base mismatches (or using inosines) instead of the 'proper' pairs decreases the 'reverse' reaction and improves yield. Also, performing the reaction in the presence of polynucleotide kinase (plus ATP) improves yield by phosphorylating the reaction 'byproduct' which decreases the reverse reaction rate. In certain embodiments, wherein the DNA is synthesized in a nanopore chip, as discussed below, the topoisomerase enzymes can be "bulked up" by adding additional amino acid sequences that do not impair function, e.g., ensure that they are large enough that they cannot pass through the nanopore.

One advantage of using a topoisomerase-mediated strategy is that the monomer is covalently attached to the topoisomerase, and therefore cannot "escape" to interfere with other reactions. When polymerase is used, the monomers can diffuse so the polymerases and/or the deblocking agents should be specific (e.g., selective for A vs C, for example) or alternatively, the monomers are provided by a flow so they don't have a chance to mix.

In one aspect, the invention provides a topoisomerase charged with a single nucleotide, i.e., a topoisomerase conjugated to a single nucleotide, e.g., wherein the topoisomerase is conjugated via the 3'-phosphate of the nucleotide, and the nucleotide is protected, e.g., phosphorylated, at the 5'-position.

The topoisomerase used in the methods claimed herein is selected from mutants of vaccinia topoisomerase that have weakened covalent binding to the CCCTT recognition site in the presence of increased NaCl concentrations (M-Topoisomerase). Thus, the M-Topoisomerase allow for topogation, but not charging, at increased amounts of NaCl. So the M-Topoisomerase can be charged at low NaCl concentration, but will not disrupt already-synthesized synthetic DNA chains at the higher NaCl concentration in the nanopore-mediated device.

Wild-type vaccinia topoisomerases are known and have, for example, the following sequence:

```
WILD-TYPE PROTEIN
                                               SEQ ID NO: 1
MRALFYKDGKLFTDNNFLNPVSDDNPAYEVLQHVKIPTHLTDVVVYEQTW

EEALTRLIFVGSDSKGRRQYFYGKMHVQNRNAKRDRIFVRVYNVMKRINC

FINKNIKKSSTDSNYQLAVFMLMETMFFIRFGKMKYLKENETVGLLTLKN

KHIEISPDEIVIKFVGKDKVSHEFVVHKSNRLYKPLLKLTDDSSPEEFLF

NKLSERKVYECIKQFGIRIKDLRTYGVNYTFLYNFWTNVKSISPLPSPKK

LIALTIKQTAEVVGHTPSISKRAYMATTILEMVKDKNFLDVVSKTTFDEF

LSIVVDHVKSSTDG
```

This sequence is encoded by the following DNA

```
WILD-TYPE DNA
                                               SEQ ID NO: 2
ATGCGTGCACTTTTTTATAAAGATGGTAAACTCTTTACCGATAATAATTT

TTTAAATCCTGTATCAGACGATAATCCAGCGTATGAGGTTTTGCAACATG

TTAAAATTCCTACTCATTTAACAGATGTAGTAGTATATGAACAAACGTGG

GAAGAGGCATTAACTAGATTAATTTTTGTGGGAAGCGATTCAAAAGGACG

TAGACAATACTTTTACGGAAAAATGCATGTACAGAATCGCAACGCTAAAA

GAGATCGTATTTTTGTTAGAGTATATAACGTTATGAAACGAATTAATTGT

TTTATAAACAAAAATATAAAGAAATCGTCCACAGATTCCAATTATCAGTT

GGCGGTTTTTATGTTAATGGAAACTATGTTTTTTATTAGATTTGGTAAAA

TGAAATATCTTAAGGAGAATGAAACAGTAGGGTTATTAACACTAAAAAAT

AAACACATAGAAATAAGTCCCGATGAAATAGTTATCAAGTTTGTAGGAAA

GGACAAAGTTTCACATGAATTTGTTGTTCATAAGTCTAATAGACTATATA

AACCGCTATTGAAACTGACGGATGATTCTAGTCCCGAAGAATTTCTGTTC

AACAAACTAAGTGAACGAAAGGTATACGAATGTATCAAACAGTTTGGTAT

TAGAATCAAGGATCTCCGAACGTATGGAGTCAATTATACGTTTTTATATA

ATTTTTGGACAAATGTAAAGTCCATATCTCCTCTTCCGTCACCAAAAAAG

TTAATAGCGTTAACTATCAAACAAACTGCTGAAGTGGTAGGTCATACTCC

ATCAATTTCAAAAAGAGCTTACATGGCAACGACTATTTTAGAAATGGTAA

AGGATAAAAATTTTTTAGATGTAGTATCTAAAACTACGTTCGATGAATTC

CTATCTATAGTCGTAGATCACGTTAAATCATCTACGGATGGA
```

The M-Topoisomerase comprises mutations weakened covalent binding to the CCCTT recognition site in the presence of increased NaCl concentrations, e.g., in the N-terminal DNA binding domain, particularly at positions F59, R67, Q69, Y70, Y72, G73, and R80, e.g., as described in Reed, et al., Biochem, 56:3307 (2017). Particularly preferred mutations providing salt-sensitivity include mutations at residues 67, 69, 70, and/or 80, e.g. Q69A/R80A; R67A/Q69A/R80A, or R67A/Y70A/R80A; e.g., a vaccina topoisomerase having a mutation at position 69 and/or 80, e.g., Q69A/R80A.

For example, M-Topoisomerase, as used herein, includes topoisomerase proteins comprising the following sequence:

SEQ ID NO: 3

RALFYKDGKLFTDNNFLNPVSDDNPAYEVLQHVKIPTHLTDVVVYEQTWE

EALTRLIFVGSDSKGX$_1$RX$_2$X$_3$FYGKMHVQNX$_4$NAKRDRIFVRVYNVMKR

INCFINKNIKKSSTDSNYQLAVFMLMETMFFIRFGKMKYLKENETVGLLT

LKNKHIEISPDEIVIKFVGKDKVSHEFVVHKSNRLYKPLLKLTDDSSPEE

FLFNKLSERKVYECIKQFGIRIKDLRTYGVNYTFLYNFWTNVKSISPLPS

PKKLIALTIKQTAEVVGHTPSISKRAYMATTILEMVKDKNFLDVVSKTTF

DEFLSIVVDHVKSSTDG

- wherein at least two of $X_1$, $X_2$, $X_3$, and $X_4$, are mutated from the residues in the wild type sequence (wherein $X_1$ is arginine (R), $X_2$ is glutamine (Q), $X_3$ is tyrosine (Y), and $X_4$ is arginine (R)) to glycine (G), alanine (A) or valine (V); provided that where only two residues are mutated,
- $X_1$ and $X_2$ are not both mutated to A;
- for example at least three or all of four of $X_1$, $X_2$, $X_3$, and $X_4$ are mutated to A;
- for example, wherein
- $X_2$ and $X_4$ are A; or
- $X_1$, $X_2$, and $X_4$ are A; or
- $X_1$, $X_3$, and $X_4$ are A.

The M-Topoisomerase may also comprise isolation sequences (for example terminal poly-histidine tags, FLAG tags (i.e., having the sequence DYKDDDDK), and/or other sequences to facilitate isolation). For example, in one embodiment, the M-Topoisomerase is

MUTANT PROTEIN

SEQ ID NO: 4

MKHHHHHHGGGSGDYKDDDDKGGGGSGRALFYKDGKLFTDNNFLNPVSDD

NPAYEVLQHVKIPTHLTDVVVYEQTWEEALTRLIFVGSDSKGRRAYFYGK

MHVQNANAKRDRIFVRVYNVMKRINCFINKNIKKSSTDSNYQLAVFMLME

TMFFIRFGKMKYLKENETVGLLTLKNKHIEISPDEIVIKFVGKDKVSHEF

VVHKSNRLYKPLLKLTDDSSPEEFLENKLSERKVYECIKQFGIRIKDLRT

YGVNYTFLYNFWTNVKSISPLPSPKKLIALTIKQTAEVVGHTPSISKRAY

MATTILEMVKDKNFLDVVSKTTFDEFLSIVVDHVKSSTDG

In this sequence, the underlined sections correspond exactly to the wild-type protein of SEQ ID NO: 1, but there is a His-Tag and a FLAG tag sequence inserted at the N-terminus (and therefore not underlined). There are two alanine mutations (Q69A/R80A), in bold and not underlined.

The M-Topoisomerase may be codon-optimized, for improved expression in a bacterial cell, e.g., in *E. coli,* or other desired expression vector. Different organisms exhibit bias towards using certain codons over others to encode the same amino acid. For example, the following is a codon-optimized sequence for expression of the M-Topoisomerase of SEQ ID NO: 4 in *E. coli:*

MUTANT DNA (expression clone)

SEQ ID NO: 5

ATGAAACACCATCATCACCATCACGGCGGCGGCTCTGGCGATTACAAAGA

CGATGACGACAAGGGTGGTGGCGGCTCCGGTCGCGCGCTGTTCTATAAGG

ATGGTAAACTGTTTACCGACAACAATTTCCTGAACCCGGTGAGCGACGAT

AATCCGGCGTACGAAGTGCTGCAACACGTGAAAATTCCGACGCACCTGAC

CGACGTTGTTGTGTACGAGCAAACCTGGGAAGAAGCGCTGACGCGCCTGA

TTTTTGTCGGTAGCGACAGCAAGGGTCGTCGTGCATACTTTTATGGTAAA

ATGCACGTTCAGAATGCGAACGCAAAGCGTGATCGTATCTTCGTCCGTGT

GTATAATGTTATGAAGCGCATTAATTGTTTCATCAACAAGAACATCAAGA

AAAGCTCGACGGATAGCAATTACCAGCTGGCCGTGTTCATGTTGATGGAA

ACCATGTTCTTTATTCGTTTCGGTAAGATGAAATACCTGAAAGAAAACGA

AACCGTCGGTCTGTTGACGCTGAAGAATAAGCATATCGAGATCAGCCCGG

ATGAAATTGTTATCAAGTTCGTTGGCAAAGACAAAGTTTCCCACGAATTC

GTCGTCCACAAGAGCAATCGTCTGTACAAGCCGCTGCTGAAGTTGACCGA

CGACAGCAGCCCAGAAGAATTTCTGTTTAACAAACTGAGCGAGCGTAAAG

TGTATGAGTGCATTAAGCAATTTGGCATTCGCATCAAAGATTTGCGTACC

TACGGTGTCAACTACACTTTCCTCTATAACTTCTGGACTAACGTTAAATC

TATTAGCCCGCTGCCGAGCCCTAAAAAGTTAATCGCCCTGACCATCAAAC

AGACCGCTGAAGTTGTGGGCCACACGCCGTCTATTAGCAAGCGTGCATAT

ATGGCGACCACGATCCTGGAAATGGTTAAAGATAAGAATTTTCTGGACGT

CGTTAGCAAAACCACGTTTGATGAGTTCCTGAGCATTGTCGTGGACCATG

TGAAATCCAGCACCGATGGT

The invention provides in another embodiment a nucleic acid encoding an M-Topoisomerase (e.g., wherein the M-Topoisomerase is a vaccina topoisomerase comprising mutations at residues 67, 69, 70, and/or 80, e.g., Q69A/R80A; R67A/Q69A/R80A, or R67A/Y70A/R80A; e.g., a vaccina topoisomerase having a mutation at position 69 and/or 80, e.g., Q69A/R80A; e.g., a topoisomerase protein comprising SEQ ID NO 3; e.g., wherein the M-Topoisomerase comprises isolation sequences; e.g., a topoisomerase protein comprising SEQ ID 4), e.g., wherein the nucleic acid is codon-optimized for expression in a bacterial host, e.g., a nucleic acid of SEQ ID NO 5.

The invention provides in another embodiment a bacterial cell expressing a nucleic acid encoding an M-Topoisomerase (e.g., wherein the M-Topoisomerase encoded is a vaccina topoisomerase comprising mutations at residues 67, 69, 70, and/or 80, e.g., Q69A/R80A; R67A/Q69A/R80A, or R67A/Y70A/R80A; e.g., a vaccina topoisomerase having a mutation at position 69 and/or 80, e.g., Q69A/R80A; e.g., a topoisomerase protein comprising SEQ ID NO: 3; e.g., wherein the M-Topoisomerase comprises isolation sequences; e.g., a topoisomerase protein comprising SEQ ID NO: 4); e.g., wherein the nucleic acid is codon-optimized for expression in a bacterial host, e.g., a nucleic acid of SEQ ID NO: 5.

The invention also provides a method for making a M-Topoisomerase comprising expressing a nucleic acid encoding an M-Topoisomerase (e.g., wherein the M-Topoisomerase is a vaccina topoisomerase comprising mutations at residues 67, 69, 70, and/or 80, e.g., Q69A/R80A; R67A/

Q69A/R80A, or R67A/Y70A/R80A; e.g., a vaccina topoisomerase having a mutation at position 69 and/or 80, e.g., Q69A/R80A; e.g., a topoisomerase protein comprising SEQ ID NO: 3; e.g., wherein the M-Topoisomerase comprises isolation sequences; e.g., a topoisomerase protein comprising SEQ ID NO: 4), e.g., wherein the nucleic acid is codon-optimized for expression in a bacterial host, e.g., a nucleic acid of SEQ ID NO: 5; in a host cell culture, e.g., in a bacterial host cell culture, e.g., in E. coli, and isolating the protein thus expressed.

For example, the invention provides in one embodiment, a method for synthesizing DNA comprising reacting a donor DNA comprising an M-topoisomerase bound to the 3' phosphate of a terminal 5'-(C/T)CCTT-3' sequence of the donor DNA with an acceptor DNA, so that the donor and acceptor DNA are ligated thereby and the M-topoisomerase is released, then dephosphorylating the 5' terminal of the ligated DNA using a phosphatase, reacting the dephosphorylated DNA with a further donor DNA sequence comprising an M-topoisomerase bound to the 3' phosphate of a terminal 5'-(C/T)CCTT-3' sequence, to obtain a further ligated DNA, and repeating until the desired sequence is obtained, wherein the M-Topoisomerase exhibits weakened covalent binding to the CCCTT recognition site in the presence of increased NaCl concentrations (e.g., wherein the M-Topoisomerase is a vaccina topoisomerase comprising mutations at residues 67, 69, 70, and/or 80, e.g., Q69A/R80A; R67A/Q69A/R80A, or R67A/Y70A/R80A; e.g., a vaccina topoisomerase having a mutation at position 69 and/or 80, e.g., Q69A/R80A; e.g., a topoisomerase protein comprising SEQ ID NO: 3; e.g., wherein the M-Topoisomerase comprises isolation sequences; e.g., a topoisomerase protein comprising SEQ ID NO: 4), and wherein the reaction takes place in an aqueous medium wherein the NaCl concentration is greater than 200 mM, e.g., 200-1000 mM, e.g., 400-600 mM, e.g., about 500 mM.

For example, in on embodiment, the method may comprise forming an M-topoisomerase bound to the 3' phosphate of a terminal 5'-(C/T)CCTT-3' sequence of the donor DNA under low salt concentration, e.g., by combining the M-topoisomerase with the donor DNA having a terminal 5'-(C/T)CCTT-3' sequence in an aqueous medium having NaCl concentration of less than 200 mM, e.g., about 25-150 mM, e.g., about 50, 100, or 150 mM, then reacting the charged donor DNA thus produced with an acceptor DNA sequence under high salt concentration, e.g., in an aqueous medium wherein the NaCl concentration is greater than 200 mM, e.g., 200-1000 mM, e.g., 400-600 mM, e.g., about 500 mM (e.g., wherein the M-Topoisomerase exhibits weakened covalent binding to the CCCTT recognition site in the presence of increased NaCl concentrations (e.g., wherein the M-Topoisomerase is a vaccina topoisomerase comprising mutations at residues 67, 69, 70, and/or 80, e.g., Q69A/R80A; R67A/Q69A/R80A, or R67A/Y70A/R80A; e.g., a vaccina topoisomerase having a mutation at position 69 and/or 80, e.g., Q69A/R80A; e.g., a topoisomerase protein comprising SEQ ID NO: 3; e.g., wherein the M-Topoisomerase comprises isolation sequences; e.g., a topoisomerase protein comprising SEQ ID NO: 4).

The invention provides in one embodiment, a method (Method A) of synthesizing a DNA molecule using topoisomerase-mediated ligation, by adding single nucleotides or oligomers to a DNA strand in the 3' to 5' direction, comprising (i) reacting a DNA molecule with a M-Topoisomerase charged with the desired nucleotide or oligomer wherein the nucleotide or oligomer is blocked from further addition at the 5' end, then (ii) deblocking the 5' end of the DNA thus formed, and repeating steps (i) and (ii) until the desired nucleotide sequence is obtained, wherein the M-Topoisomerase exhibits weakened covalent binding to the 5'-(C/T)CCTT-3', e.g., 5'-CCCTT-3' recognition site in the presence of increased NaCl concentrations, relative to a wild-type topoisomerase, e.g., A1.1. Method A which is a method of synthesizing a DNA molecule by adding single nucleotides in the 3' to 5' direction comprising (i) reacting a DNA molecule with a topoisomerase charged with the desired nucleotide in 5'protected form, e.g., 5'phosphorylated form, such that the desired nucleotide in 5'protected form is added to the 5' end of the DNA, then (ii) deprotecting the 5' end of the DNA thus formed through the use of a phosphatase enzyme, and repeating steps (i) and (ii) until the desired nucleotide sequence is obtained; or A1.2. Method A which is a method of synthesizing a DNA molecule by adding oligomers in the 3' to 5' direction comprising (i) reacting a DNA molecule with a topoisomerase charged with the desired oligomer, thereby ligating the oligomer to the DNA molecule, then (ii) using a restriction enzyme to provide a 5' site for a topoisomerase-mediated ligation for another oligomer, and repeating steps (i) and (ii) until the desired oligomer sequence is obtained.

A1.3. Any foregoing method comprising providing ligase and ATP to seal nicks in the DNA [NB: the topoisomerase ligation only ligates one strand].

A1.4. Any foregoing method wherein the topoisomerase-charged donor oligonucleotide comprises a 5' overhang on the strand complementary to the strand bearing the topoisomerase, comprising a polyinosine sequence [NB: inosines act as 'universal bases' and pair with any other base].

A1.5. Any foregoing method wherein the restriction enzyme is a type IIS restriction enzyme which can cleave all of the added DNA with the exception of a single base (the base which is being 'added').

A1.6. Any foregoing method wherein the topoisomerase is selected from vaccinia topoisomerase and SVF topoisomerase I.

A1.7. Any foregoing method wherein vaccinia topoisomerase (which recognizes (C/T)CCTT) is used to add dTTP nucleotides and SVF topoisomerase I (which recognizes CCCTG) is used to add dGTP nucleotides, e.g., to provide binary code A1.8. Any foregoing method wherein the DNA is double stranded and the reserve chamber further comprises a ligase, e.g., NAD dependent ligase, and ATP, to repair the DNA strand not joined by the topoisomerase.

A1.9. Any foregoing method comprising use of a topoisomerase inhibitor to suppress binding and activity of free topoisomerase to the DNA oligomer, e.g., wherein the inhibitors is selected from novobiocin and coumermycin.

A1.10. Any foregoing method wherein the DNA strand thus provided has a sequence comprising thymidine (T) nucleosides and deoxyguanosine (G) nucleosides.

A1.11. Any foregoing method wherein the topoisomerase adds a single base, but the restriction enzyme cleaves at a position which is one nucleotide in the 5' direction from the base added by topoisomerase.

A1.12. Any foregoing method wherein the DNA strand thus provided has a sequence comprising a sequence of 'TT' and 'TG' dinucleotides.

A1.13. Any foregoing method wherein the DNA is single stranded,

A1.14. Any foregoing method wherein the DNA double stranded.

A1.15. Any foregoing method wherein the DNA is on a substrate or magnetic bead, where it can be selectively exposed to or removed from the reagents as required to provide the desired sequence.

A1.16. Any foregoing method wherein some or all of the reagents for adding or deblocking the DNA are supplied by flow and removed by flushing.

A1.17. Any foregoing method wherein the attachment of the single nucleotides or oligomers to a single-stranded DNA is facilitated by the presence of an adapter DNA having sequences to which the topoisomerase and the single stranded acceptor DNA can bind.

A1.18. Any foregoing method carried out in a system (i) where a nanopore separates a chamber comprising the topoisomerase from a chamber comprising the phosphatase or restriction enzyme, wherein the nanopore allows movement of the DNA by electrical attraction, but not the enzymes, e.g. as described in any of Method B, et seq. or (ii) where the DNA is anchored to a substrate, e.g., a magnetic bead, to allow transfer of the DNA to A1.19. Any foregoing method wherein the M-Topoisomerase is a vaccinia topoisomerase having mutations at residues 67, 69, 70, and/or 80, e.g., Q69A/R80A; R67A/Q69A/R80A, or R67A/Y70A/R80A; e.g., a vaccina topoisomerase having a mutation at position 69 and/or 80, e.g., Q69A/R80A.

A1.20. Any foregoing method wherein the M-Topoisomerase is a mutant of SEQ ID NO: 1 exhibiting weakened covalent binding to the CCCTT recognition site in the presence of increased NaCl concentrations, relative to a wild-type topoisomerase of SEQ ID NO: 1.

A1.21. Any foregoing method wherein the M-Topoisomerase is a mutant of SEQ ID NO: 1 exhibiting weakened covalent binding to the CCCTT recognition site in the presence of increased NaCl concentrations, relative to a wild-type topoisomerase of SEQ ID NO: 1, wherein the mutation(s) comprise a mutation at residue at residues 67, 69, 70, and/or 80, e.g., a mutation to alanine at residues 67, 69, 70, and/or 80.

A1.22. Any foregoing method wherein the M-Topoisomerase is a mutant of SEQ ID NO: 1 exhibiting weakened covalent binding to the CCCTT recognition site in the presence of increased NaCl concentrations, relative to a wild-type topoisomerase of SEQ ID NO: 1, wherein the mutation(s) comprise Q69A and/or R80A.

A1.23. Any foregoing method wherein the M-Topoisomerase is a mutant of SEQ ID NO: 1 exhibiting weakened covalent binding to the CCCTT recognition site in the presence of increased NaCl concentrations, relative to a wild-type topoisomerase of SEQ ID NO: 1, wherein the mutation(s) comprise Q69A/R80A; R67A/Q69A/R80A, or R67A/Y70A/R80A.

A1.24. Any foregoing method wherein the M-Topoisomerase is a mutant of SEQ ID NO: 1 exhibiting weakened covalent binding to the CCCTT recognition site in the presence of increased NaCl concentrations, relative to a wild-type topoisomerase of SEQ ID NO: 1, wherein the mutation(s) comprise Q69A and R80A.

A1.25. Any foregoing method wherein the M-Topoisomerase comprises SEQ ID NO: 3, as hereinbefore described.

A1.26. Any foregoing method wherein the M-Topoisomerase comprises a terminal purification tag, e.g., a poly-histidine tag or a FLAG tag.

A1.27. Any foregoing method wherein the M-Topoisomerase comprises SEQ ID NO: 4, or a conservatively modified variant thereof.

A1.28. Any foregoing method wherein the M-Topoisomerase comprises SEQ ID NO: 4.

A1.29. Any foregoing method wherein the step of reacting a DNA molecule with a M-Topoisomerase charged with the desired nucleotide or oligomer is carried out in a medium having NaCl concentration of greater than 100 mM, e.g., greater than 200 mM, e.g., 200-1000 mM, e.g. 200-300 mM, or 400-600 mM, e.g., about 500 mM.

A1.30. Any foregoing method wherein the M-Topoisomerase charged with the desired nucleotide or oligomer is formed by combining the M-topoisomerase with the donor DNA having a terminal 5'-(C/T)CCTT-3' sequence in an aqueous medium having NaCl concentration of less than 200 mM, e.g., 25-150 mM, e.g., about 50, 100, or 150 mM.

One possible concern is poly-G sequences may form G-quartet secondary structures. By moving the restriction enzyme back one base (to the 5' of the topo sequence) and following a similar Topo/IIS strategy a 'TT' or 'TG' can be added, each of which can represent a different bit. While this would require 2 bases to encode a bit, it has the advantage of avoiding poly-G sequences. In other embodiments, other bases in the 3' end of the topo recognition sequence—although less efficient than (C/T)CCTT, can allow conjugation using poxvirus topoisomerase with (C/T)CCTA, (C/T)CCTC and (C/T)CCTG. Protein engineering/selection techniques can be used to improve the efficiency of these reactions as well, and similar approaches can be used to add non-canonical bases.

In certain embodiments, the method of synthesizing DNA by this method includes treating the DNA with a ligase and ATP. The topoisomerase only joins together one side of the DNA (the other is essentially nicked). The ligase would repair the nick and ensure that the topoisomerase itself doesn't recut the reaction product and cleave it.

In certain embodiments, the method comprises using a topoisomerase inhibitor to suppress binding and activity of free topoisomerase to the DNA oligomer. Suitable inhibitors include novobiocin and coumermycin. Note that complete inhibition is not desirable, as a low level of topoisomerase activity can help 'relax' coiled DNA, which is useful especially when synthesizing long DNA chains.

Thus, in another embodiment, the disclosure provides a method (Method B) for synthesizing DNA in a nanochip, comprising one or more addition chambers containing a M-Topoisomerase-charged oligonucleotide (i.e., oligonucleotide bound at the 3' end to a M-Topoisomerase), and one or more reserve chambers comprising a restriction enzyme or deblocker, e.g., phosphatase, said chambers also containing compatible buffer solution and being separated by a membrane comprising at least one nanopore, wherein the topoisomerase and the restriction enzyme are prevented from passing through the nanopore (e.g., because they are too large and/or because they are tethered to a substrate in the first and second chambers respectively), the synthesis being carried out by a cycle of adding single nucleotides or short oligonucleotide blocks to a first end of a nucleic acid having a first end and a second end, wherein the first end of the nucleic acid is moved by electrical attraction between an addition chambers and a reserve chamber, for example in one embodiment as follows:
- (i) moving the 5' end of a receiver DNA (e.g., a double-stranded DNA) into a first addition chamber, by means of an electrical force,
- (ii) providing in the first addition chamber a topoisomerase-charged donor oligonucleotide, wherein the donor oligonucleotide comprises a topoisomerase binding site, an informational sequence (e.g., selected from at least two different nucleotides or sequences, e.g., wherein one sequence corresponds to '0' and the other to '1' in a binary code), and a restriction site which when cleaved by a restriction enzyme will yield a topoisomerase ligation site;
- (iii) allowing sufficient time for the donor oligonucleotide to ligate to and thereby extend the receiver DNA;
- (iv) moving the 5' end of the receiver DNA thus extended into the reserve chamber, by means of an electrical force, e.g., so that the restriction enzyme cleaves the receiver DNA to provide a topoisomerase ligation site, or in the case of single nucleotide addition, the deblocker, e.g., phosphatase, generates a 5' unblocked nucleotide on the single stranded DNA; and
- (v) repeating the cycle of steps (i)-(iv), adding oligonucleotides having the same or different informational sequence, until the desired DNA sequence or sequences are obtained;

wherein the M-Topoisomerase exhibits weakened covalent binding to the CCCTT recognition site in the presence of increased NaCl concentrations.

For example, the invention provides

B.1. Method B wherein the 3' end of the receiver DNA is attached proximate to a nanopore and the 5'end of the receiver oligonucleotide comprises a topoisomerase ligation site, and comprising a step after step (iv) of adding an additional oligonucleotide to the 5' end of the receiver DNA by flushing the first addition chamber and providing new topoisomerase-charged donor oligonucleotide to the first addition chamber, wherein the new donor oligonucleotide has a different informational sequence from the previous donor oligonucleotide; and if desired that the new donor oligonucleotide be added to the receiver DNA, drawing the 5' end of the receiver nucleic acid back into the first chamber, and repeating steps (i)-(iii), or if not so desired, allowing the receiver DNA to remain in the second chamber until the desired donor oligonucleotide is provided to the first chamber.

B.2. Any foregoing method wherein a multiplicity of receiver DNA molecules are synthesized independently in parallel, such that DNA molecules having different sequences are obtained by separately controlling whether they are present in the first chamber.

B.3. Any foregoing method wherein a multiplicity of receiver DNA molecules each bound at the 3' end to a surface proximate to a nanopore are synthesized independently, wherein each nanopore has an associated pair of electrodes, wherein one electrode in the pair is located proximate to one end of the nanopore and the other electrode located proximate to the other end of the nanopore, such that each receiver DNA molecule can be independently moved between the first and second chamber by current provided by the pair of electrodes.

B.4. Any foregoing method wherein the donor oligonucleotides used in step (i) of the cycle alternate with each cycle between donor oligonucleotides comprising a first informational sequence and donor oligonucleotides comprising a second informational sequence.

B.5. Method 2 comprising the step of adding an additional oligonucleotide to the 5' end of the receiver DNA by returning the 5' end of the receiver DNA to the first addition chamber to add an oligonucleotide having the same informational sequence or moving the 5' end of the receiver DNA to a second addition chamber to having a donor oligonucleotide bound at the 3' end to a topoisomerase, wherein the donor oligonucleotide in the second addition chamber has a different informational sequence from the donor oligonucleotide in the first addition chamber.

B.6. Any foregoing method wherein the donor oligonucleotide comprises a structure as follows:

```
                                       (SEQ ID NO: 6)
5' CGAAGGG <Informational sequence A or B>

GTCGACNNNNN

3' GCTTCCC <---------Complement---------->

CAGCTGNNNNN
``` wherein N refers to any nucleotide and the restriction enzyme is Acc1, which can cut the DNA (e.g., GTCGAC in the above sequence) so as to provide an appropriate overhang.

B.7. Any foregoing method wherein the donor oligonucleotide has a hairpin structure, e.g., 2.6 wherein the NNNNN groups on the top and bottom strands are joined.

B.8. Any foregoing method wherein at least one of the topoisomerase charged oligonucleotides has a structure as follows:

```
                                       (SEQ ID NO: 6)
5' CGAAGGG <Informational sequence A or B>

GTCGACNNNNN

3' *TTCCC <---------Complement---------->

CAGCTGNNNNN
(*= topoisomerase)
```

B.9. Any foregoing method wherein at least one of the topoisomerase charged oligonucleotides has a structure as follows:

```
                                       (SEQ ID NO: 7)
    5' pCACGTCAGGCGTATCCATCCCTT*

3' GTGCAGTCCGCATAGGTAGGGAAGCGC
```

B.10. The preceding method wherein the topoisomerase charged oligonucleotide

B.11. Any foregoing method wherein the sequence of DNA synthesized is determined following each cycle by detecting the change in electric potential, current, resistance, capacitance and/or impedance as the oligonucleotide passes through the nanopore.

B.12. Any foregoing method wherein the synthesis of the DNA takes place in a buffer solution, e.g., a solution comprising a buffer for pH 7-8.5, e.g., ca. pH 8, e.g., a buffer comprising tris(hydroxymethyl)aminomethane (Tris), a suitable acid, and optionally a chelater, e.g., ethylenediaminetetraacetic acid (EDTA), for example TAE buffer containing a mixture of Tris base, acetic acid and EDTA or TBE buffer comprising a mixture of Tris base, boric acid and EDTA; for example a solution comprising 10 mM Tris pH 8, 1 mM EDTA, 150 mM KCl, or for example, 50 mM Potassium Acetate, 20 mM Tris-acetate, 10 mM Magnesium Acetate, pH 7.9 @ 25° C.

B.13. Any foregoing method further comprising removing the DNA from the nanochip.

B.14. Any foregoing method further comprising amplifying the DNA thus synthesized.

B.15. Any foregoing method further comprising removing the DNA from the nanochip and crystallizing the DNA.

B.16. Any foregoing method further comprising stabilizing the DNA, e.g., by drying a solution comprising the DNA together with one or more of a buffer (e.g., a borate buffer), an antioxidant, a humectant, e.g., a polyol, and optionally a chelator, for example as described in U.S. Pat. No. 8,283,165 B2, incorporated herein by reference, or by forming a matrix between the nucleic acid and a polymer, such as poly(ethylene glycol)-poly(1-lysine) (PEG-PLL) AB type block copolymer.

B.17. Any foregoing method comprising providing ligase and ATP to seal nicks in the DNA [NB: the topoisomerase ligation only ligates one strand].

B.18. Any foregoing method wherein the topoisomerase-charged donor oligonucleotide comprises a 5' overhang on the strand complementary to the strand bearing the topoisomerase, comprising a polyinosine sequence [NB: inosines act as 'universal bases' and pair with any other base].

B.19. Any foregoing method wherein the restriction enzyme is a type IIS restriction enzyme which can cleave all of the added DNA with the exception of a single base (the base which is being 'added').

B.20. Any foregoing method wherein the topoisomerase is selected from vaccinia topoisomerase and SVF topoisomerase I.

B.21. Any foregoing method wherein vaccinia topoisomerase (which recognizes (C/T)CCTT) is used to add dTTP nucleotides and SVF topoisomerase I (which recognizes CCCTG) is used to add dGTP nucleotides, e.g., to provide binary code information.

B.22. Any foregoing method wherein the reserve chamber further comprises a ligase and ATP, to repair the DNA strand not joined by the topoisomerase.

B.23. Any foregoing method comprising use of a topoisomerase inhibitor to suppress binding and activity of free topoisomerase to the DNA oligomer, e.g., wherein the inhibitors is selected from novobiocin and coumermycin.

B.24. Any foregoing method wherein the DNA strand thus provided has a sequence comprising thymidine (T) nucleosides and deoxyguanosine (G) nucleosides.

B.25. Any foregoing method wherein the topoisomerase adds a single base, but the restriction enzyme cleaves at a position which is one nucleotide in the 5' direction from the base added by topoisomerase.

B.26. Any foregoing method wherein the DNA strand thus provided has a sequence comprising a sequence of 'TT' and 'TG' dinucleotides.

B.27. Any foregoing method which is a method of synthesizing a DNA molecule by adding single nucleotides in the 3' to 5' direction comprising (i) reacting a DNA molecule with a topoisomerase charged with the desired nucleotide in 5'protected form, e.g., 5'phosphorylated form, such that the desired nucleotide in 5'protected form is added to the 5' end of the DNA, then (ii) deprotecting the 5' end of the DNA thus formed through the use of a phosphatase enzyme, and repeating steps (i) and (ii) until the desired nucleotide sequence is obtained.

B.28. Any foregoing method which is a method of synthesizing a DNA molecule by adding oligomers in the 3' to 5' direction comprising (i) reacting a DNA molecule with a topoisomerase charged with the desired oligomer, thereby ligating the oligomer to the DNA molecule, then (ii) using a restriction enzyme to provide a 5' site for a topoisomerase-mediated ligation for another oligomer, and repeating steps (i) and (ii) until the desired nucleotide sequence is obtained.

B.29. Any foregoing method wherein the M-Topoisomerase is a vaccinia topoisomerase having mutations at residues 67, 69, 70, and/or 80, e.g., Q69A/R80A; R67A/Q69A/R80A, or R67A/Y70A/R80A; e.g., a vaccina topoisomerase having a mutation at position 69 and/or 80, e.g., Q69A/R80A.

B.30. Any foregoing method wherein the M-Topoisomerase is a mutant of SEQ ID NO: 1 exhibiting weakened covalent binding to the CCCTT recognition site in the presence of increased NaCl concentrations, relative to a wild-type topoisomerase of SEQ ID NO: 1.

B.31. Any foregoing method wherein the M-Topoisomerase is a mutant of SEQ ID NO: 1 exhibiting weakened covalent binding to the CCCTT recognition site in the presence of increased NaCl concentrations, relative to a wild-type topoisomerase of SEQ ID NO: 1, wherein the mutation(s) comprise a mutation at residue at residues 67, 69, 70, and/or 80, e.g., a mutation to alanine at residues 67, 69, 70, and/or 80.

B.32. Any foregoing method wherein the M-Topoisomerase is a mutant of SEQ ID NO: 1 exhibiting weakened covalent binding to the CCCTT recognition site in the presence of increased NaCl concentrations, relative to a wild-type topoisomerase of SEQ ID NO: 1, wherein the mutation(s) comprise Q69A and/or R80A.

B.33. Any foregoing method wherein the M-Topoisomerase is a mutant of SEQ ID NO: 1 exhibiting weakened covalent binding to the CCCTT recognition site in the presence of increased NaCl concentrations, relative to a wild-type topoisomerase of SEQ ID NO: 1, wherein the mutation(s) comprise Q69A/R80A; R67A/Q69A/R80A, or R67A/Y70A/R80A.

B.34. Any foregoing method wherein the M-Topoisomerase is a mutant of SEQ ID NO: 1 exhibiting weakened covalent binding to the CCCTT recognition site in the presence of increased NaCl concentrations, relative to a wild-type topoisomerase of SEQ ID NO: 1, wherein the mutation(s) comprise Q69A and R80A.

B.35. Any foregoing method wherein the M-Topoisomerase comprises SEQ ID NO: 3, as hereinbefore described.

B.36. Any foregoing method wherein the M-Topoisomerase comprises a terminal purification tag, e.g., a poly-histidine tag or a FLAG tag.

B.37. Any foregoing method wherein the M-Topoisomerase comprises SEQ ID NO: 4, or a conservatively modified variant thereof.

B.38. Any foregoing method wherein the M-Topoisomerase comprises SEQ ID NO: 4.

B.39. Any foregoing method wherein the DNA synthesis is carried out as described in any of WO 2017/151680, published Sep. 8, 2017, WO 2018/081745, published May 3, 2018, and U.S. application Ser. No. 15/969,745, filed May 2, 2018, the entire contents of which applications are incorporated herein by reference, using M-Topoisomerase instead of wild-type topoisomerase to ligate the nucleotides or oligonucleotides to the DNA strand.

B.40. Any foregoing method wherein the buffer solution in the chambers has an NaCl concentration of greater than 100 mM, e.g., greater than 200 mM, e.g., e.g., 200-1000 mM, e.g., 200-300 mM, or 400-600 mM, e.g., about 500 mM.

B.41. Any foregoing method wherein the M-Topoisomerase-charged oligonucleotide is pre-formed by combining the M-topoisomerase with a donor DNA having a terminal 5'-(C/T)CCTT-3' sequence in an aqueous medium having NaCl concentration of less than 200 mM, e.g., 25-150 mM, e.g., about 50, 100, or 150 mM.

B.42. Any foregoing method which is a method in accordance with any of Method A, et seq.

The product of the synthesis reactions can be detected, reviewed for quality control purposes, and read to extract the data encoded on the polymer. For example the DNA may be amplified and sequenced by conventional means to confirm that the nanopore sequencing is robust, or it may be checked by reading the sequence by measuring the capacitive variance or impedance changes (e.g., as detected in a resonant radiofrequency circuit) as the DNA molecule passes through the nanopore, wherein the changes correspond to different bases.

In another embodiment, the invention provides an oligonucleotide comprising a topoisomerase binding site, an informational sequence (e.g., selected from at least two different sequences, e.g., wherein one sequence corresponds to '0' and the other to '1' in a binary code), and a restriction site which when cleaved by a restriction enzyme will yield a topoisomerase ligation site, e.g., comprising the following sequence:

```
                                          (SEQ ID NO: 8)
5' CGAAGGG <Informational sequence A or B>

GTCGAC

3' GCTTCCC <---------Complement---------->

CAGCTG
``` wherein the Informational Sequence A or B is a sequence of 3-12, e.g., about 8 nucleotides, for use in any of the foregoing Methods A or B.

In another embodiment, the invention provides a topoisomerase charged oligonucleotide wherein the oligonucleotide comprises a topoisomerase binding site, an informational sequence (e.g., selected from at least two different sequences, e.g., wherein one sequence corresponds to '0' and the other to '1' in a binary code), and a restriction site which when cleaved by a restriction enzyme will yield a topoisomerase ligation site; for example a topoisomerase charged oligonucleotide having a structure as follows:

```
                                          (SEQ ID NO: 6)
5' CGAAGGG <Informational sequence A or B>

GTCGACNNNNN

3' *TTCCC <---------Complement---------->

CAGCTGNNNNN
``` wherein the Informational Sequence A or B is a sequence of 3-12, e.g., about 8 nucleotides and * is M-Topoisomerase covalently bound to the oligonucleotide; e.g., wherein the M-Topoisomerase is as hereinbefore described.

In another embodiment, the invention provides a M-Topoisomerase, as hereinbefore described, for use in any of the foregoing Methods A or B.

DNA strands synthesized by the methods provided herein may be read by providing an LC resonator having an effective impedance; providing a cell, the cell having a nano-pore or nano-channel and a polymer that can translocate through the nanopore or nano-channel, such translocation affecting the effective impedance, the resonator having an AC output voltage resonant frequency response at a probe frequency, which is based on the effective impedance, in response to an AC input voltage at the probe frequency; providing the AC input voltage having at least the probe frequency; and monitoring the AC output voltage at least at the probe frequency, the AC output voltage at the probe frequency being indicative of the data stored in the polymer at the time of monitoring; for example wherein the DNA comprises at least two types of nucleotides, each type of nucleotide providing a unique frequency response at the probe frequency.

The cell for use in the above reading method may comprise at least a top electrode and a bottom electrode, the nanopore or nano-channel being disposed between the electrodes, and the cell having a fluid therein, and wherein the electrodes, the nanopore or nano-channel and the fluid having an effective cell capacitance that changes when the polymer passes through the nanopore or nano-channel, e.g., wherein the effective impedance comprises an inductor connected in series with the effective capacitance to create the resonator, a combination of the inductor and effective capacitance being related to the resonant frequency response, e.g., wherein the DNA is moved through the nanopore via a DC steering voltage applied to the electrodes, e.g., wherein the cell has at least three chambers, at least two nanopores, and at least three electrodes for moving the polymer through the nanopore, e.g., wherein the probe frequency is about 1 MHz to 100 GHz, e.g., wherein the resonator comprises a longitudinal resonator and/or a transverse resonator.

The same nanopore-based device may be adapted for use in the methods herein, wherein the cell comprises one or more addition chambers or channels containing buffer solution and reagents for addition of one or more monomers or oligomers to the charged polymer in blocked form, such that only a single monomer or oligomer can be added in one reaction cycle; and one or more deblocking chambers or channels containing buffer solution and reagents for removing the blocker group from the DNA, wherein the addition chambers or channels are separated from the deblocking chambers or channels by one or more membranes comprising one or more nanopores, and wherein the DNA can pass through a nanopore and at least one of the reagents for addition of one or more monomers or oligomers (e.g., the M-Topoisomerase) cannot.

In another embodiment, the invention provides vectors and methods for Topo-cloning, incorporating DNA into a vector of interest without the need for restriction enzymes. For example, the invention provides a DNA vector, wherein the vector is in linear form and comprises a M-Topoisomerase covalently bound to the 3'phosphate at each end, and also provides a method of inserting a DNA sequence into the vector, wherein the DNA sequence has compatible ends so the DNA sequence is ligated into the vector and the topoisomerase is released. In this embodiment, the M-topoisomerase replaces the functions of a restriction enzyme and a ligase. The M-topoisomerase recognizes the pentameric sequence 5'-(C/T)CCTT-3' and forms a covalent bond with the phosphate group attached to the 3' thymidine. It cleaves one DNA strand, enabling the DNA to unwind. The enzyme then relegates the ends of the cleaved strand and releases itself from the DNA. To harness the religating activity of topoisomerase, M-topoisomerase vectors are provided linearized with M-topoisomerase covalently bound to each 3' phosphate. This enables the vectors to readily ligate DNA sequences with compatible ends.

Methods of topoisomerase cloning are known, and commercially available, e.g., from Thermo-Fischer. However, these methods of topoisomerase cloning suffer from the disadvantage that potential back reaction between free topoisomerase and DNA can reduce the efficiency of the reaction. M-topoisomerase has weakened covalent binding to the 5'-(C/T)CCTT-3', e.g., 5'-CCCTT-3' recognition site (charging) in the presence of increased NaCl concentrations, the insertion of the DNA of interest (topogation) can be carried out with elevated concentrations of NaCl, e.g., in a medium having NaCl concentration of greater than 100 mM, e.g., greater than 200 mM, e.g., 200-300 mM, or 400-600 mM, e.g., about 500 mM, thereby reducing undesired back-reactions or "re-charging" of DNA in the media and making the insertion more efficient.

In some embodiments, the vector ends are "sticky," with an overhang that is complementary to an overhang of DNA of interest to be inserted. For example, in TA Topo cloning, Taq polymerase is used to amplify the DNA of interest, so the resulting DNA will typically have an extra "A" nucleotide at the 3' end during amplification, which will be complementary to a "T" overhang on the vector, to which the M-topoisomerase is attached. The complementary T and A residues will associate, and the topoisomerase will ligate the DNA and be released.

In some embodiments, the vector ends are blunt.

In some embodiments, one end of the vector is sticky, with an overhang complementary to the DNA of interest to be inserted, and the other is blunt, thereby ensuring that the DNA of interest is inserted in a particular direction. Directional topoisomerase cloning enables cloning of blunt-ended PCR products in a 5'→3' orientation directly into a expression vector, thereby eliminating subcloning steps. For example, in some embodiments, directional topoisomerase cloning vectors contain a single-strand GTGG overhang on the 5' end and a blunt end on the 3' end. The four-nucleotide overhang invades the double-strand DNA of the PCR product and anneals to a CACC sequence in a 5' primer. The topoisomerase then ligates the PCR product in the correct orientation.

In a particular embodiment, the M-topoisomerase is the Q69A/R80A vaccinia topoisomerase double mutant.

Thus the invention provides a DNA vector (Vector M) wherein the vector is in linear form and comprises a M-Topoisomerase covalently bound to the 3'phosphate at each end. For example, the invention provides:

M1. Vector M wherein the ends of the DNA vector have a "T" overhang, e.g.,

```
-CCCTT*
-GGGA
```
and
```
AGGG-
*TTCCC-
``` wherein * represents the M-topoisomerase bound to the 3' phosphate.

M2. Vector M wherein the ends of the DNA vector are blunt, e.g.,

```
-CCCTT*
-GGGAA
```
and
```
AAGGG-
*TTCCC-
``` wherein * represents the M-topoisomerase bound to the 3' phosphate.

M3. Vector M wherein one end of the DNA vector is sticky, e.g.,

```
-CCCTT*
-GGGAAXXXX
``` wherein * represents the M-topoisomerase bound to the 3' phosphate and wherein XXXX denotes a DNA sequence complementary to a sequence at one end of the vector to be inserted, and the other end is blunt, e.g.,

```
AAGGG-
*TTCCC-
```

M4. Vector M3 wherein XXXX is GTGG.

M5. Any foregoing vector wherein the M-Topoisomerase is a vaccinia topoisomerase having mutations at residues 67, 69, 70, and/or 80, e.g., Q69A/R80A; R67A/Q69A/R80A, or R67A/Y70A/R80A; e.g., a vaccina topoisomerase having a mutation at position 69 and/or 80, e.g., Q69A/R80A.

M6. Any foregoing vector wherein the M-Topoisomerase is a mutant of SEQ ID NO: 1 exhibiting weakened covalent binding to the CCCTT recognition site in the presence of increased NaCl concentrations, relative to a wild-type topoisomerase of SEQ ID NO: 1.

M7. Any foregoing vector wherein the M-Topoisomerase is a mutant of SEQ ID NO: 1 exhibiting weakened covalent binding to the CCCTT recognition site in the presence of increased NaCl concentrations, relative to a wild-type topoisomerase of SEQ ID NO: 1, wherein the mutation(s) comprise a mutation at residue at residues 67, 69, 70, and/or 80, e.g., a mutation to alanine at residues 67, 69, 70, and/or 80.

M8. Any foregoing vector wherein the M-Topoisomerase is a mutant of SEQ ID NO: 1 exhibiting weakened covalent binding to the CCCTT recognition site in the presence of increased NaCl concentrations, relative to a wild-type topoisomerase of SEQ ID NO: 1, wherein the mutation(s) comprise Q69A and/or R80A.

M9. Any foregoing vector wherein the M-Topoisomerase is a mutant of SEQ ID NO: 1 exhibiting weakened covalent binding to the CCCTT recognition site in the presence of increased NaCl concentrations, relative to a wild-type topoisomerase of SEQ ID NO: 1, wherein the mutation(s) comprise Q69A/R80A; R67A/Q69A/R80A, or R67A/Y70A/R80A.

M10. Any foregoing vector wherein the M-Topoisomerase is a mutant of SEQ ID NO: 1 exhibiting weakened covalent binding to the CCCTT recognition site in the presence of increased NaCl concentrations, relative to a wild-type topoisomerase of SEQ ID NO: 1, wherein the mutation(s) comprise Q69A and R80A.

M11. Any foregoing vector wherein the M-Topoisomerase comprises SEQ ID NO: 3, as hereinbefore described.

M12. Any foregoing vector wherein the M-Topoisomerase comprises a terminal purification tag, e.g., a poly-histidine tag or a FLAG tag.

M13. Any foregoing vector wherein the M-Topoisomerase comprises SEQ ID NO: 4, or a conservatively modified variant thereof.

M14. Any foregoing vector wherein the M-Topoisomerase comprises SEQ ID NO: 4.

M15. Any foregoing vector wherein the M-Topoisomerase is bound to the vector (i.e., wherein the vector is charged) in an aqueous medium having NaCl concentration of less than 200 mM, e.g., about 25-150 mM, e.g., about 50, 100, or 150 mM.

The invention further provides a method (Method C) of inserting a DNA sequence of interest into a vector, without the use of restriction enzymes, wherein the vector is a vector according to any of Vector M, et seq., comprising combining the DNA sequence of interest with the vector in an aqueous medium having NaCl concentration of greater than 100 mM, e.g., greater than 200 mM, e.g., 200-1000 mM, e.g., 200-300 mM, or 400-600 mM, e.g., about 500 mM.

For example, the invention provides,

C1. Method C wherein the vector is Vector M1 and the DNA of interest has a terminal A nucleotide overhang at each 3' end.

C2. Method C1 wherein the DNA of interest is a DNA sequence which has been amplified using Taq polymerase.

C3. Method C wherein the vector is Vector M2 and the ends of the DNA of interest are blunt.

C4. Method C3 wherein the DNA of interest is a DNA sequence which has been amplified using Pfu polymerase.

C5. Method C wherein the vector is Vector M3 and one end of the DNA of interest has a sequence complementary to XXXX.

C6. Method C wherein the vector is Vector is Vector M4 and one end of the DNA of interest has an overhand with a sequence CACC.

C7. Any foregoing method wherein the DNA sequence of interest is combined with the vector in an aqueous medium having NaCl concentration of 400-600 mM, e.g., about 500 mM.

C8. Any foregoing method wherein the DNA sequence of interest is combined with the vector at room temperature.

Although the disclosure has been described herein using exemplary techniques, algorithms, or processes for implementing the present disclosure, it should be understood by those skilled in the art that other techniques, algorithms and processes or other combinations and sequences of the techniques, algorithms and processes described herein may be used or performed that achieve the same function(s) and result(s) described herein and which are included within the scope of the present disclosure.

Any process descriptions, steps, or blocks in process flow diagrams provided herein indicate one potential implementation, and alternate implementations are included within the scope of the preferred embodiments of the systems and methods described herein in which functions or steps may be deleted or performed out of order from that shown or discussed, including substantially concurrently or in reverse order, depending on the functionality involved, as would be understood by those reasonably skilled in the art.

It should be understood that, unless otherwise explicitly or implicitly indicated herein, any of the features, characteristics, alternatives or modifications described regarding a particular embodiment herein may also be applied, used, or incorporated with any other embodiment described herein. Also, the drawings herein are not drawn to scale, unless indicated otherwise.

EXAMPLES

Example 1—Characterization of the Topoisomerase "Salt Mutants"

Topoisomerase (30 pmoles) is incubated with 20 pmoles of ShuBT cassette, 50 mM Tris, pH=7.4, and the designated concentration of NaCl in a 20 ul volume for 15 minutes at 37° C. Five microliters of LDS Sample Buffer (Thermo-Fisher) is added to quench the reaction, and all of the sample is loaded onto a 4-12% Bis-Tris PAGE gel with 1×MOPS SDS running buffer (Thermo-Fisher). The gel is stained overnight with 1×One-Step Blue Protein Gel Stain (Biotium) and imaged.

Figure 2:
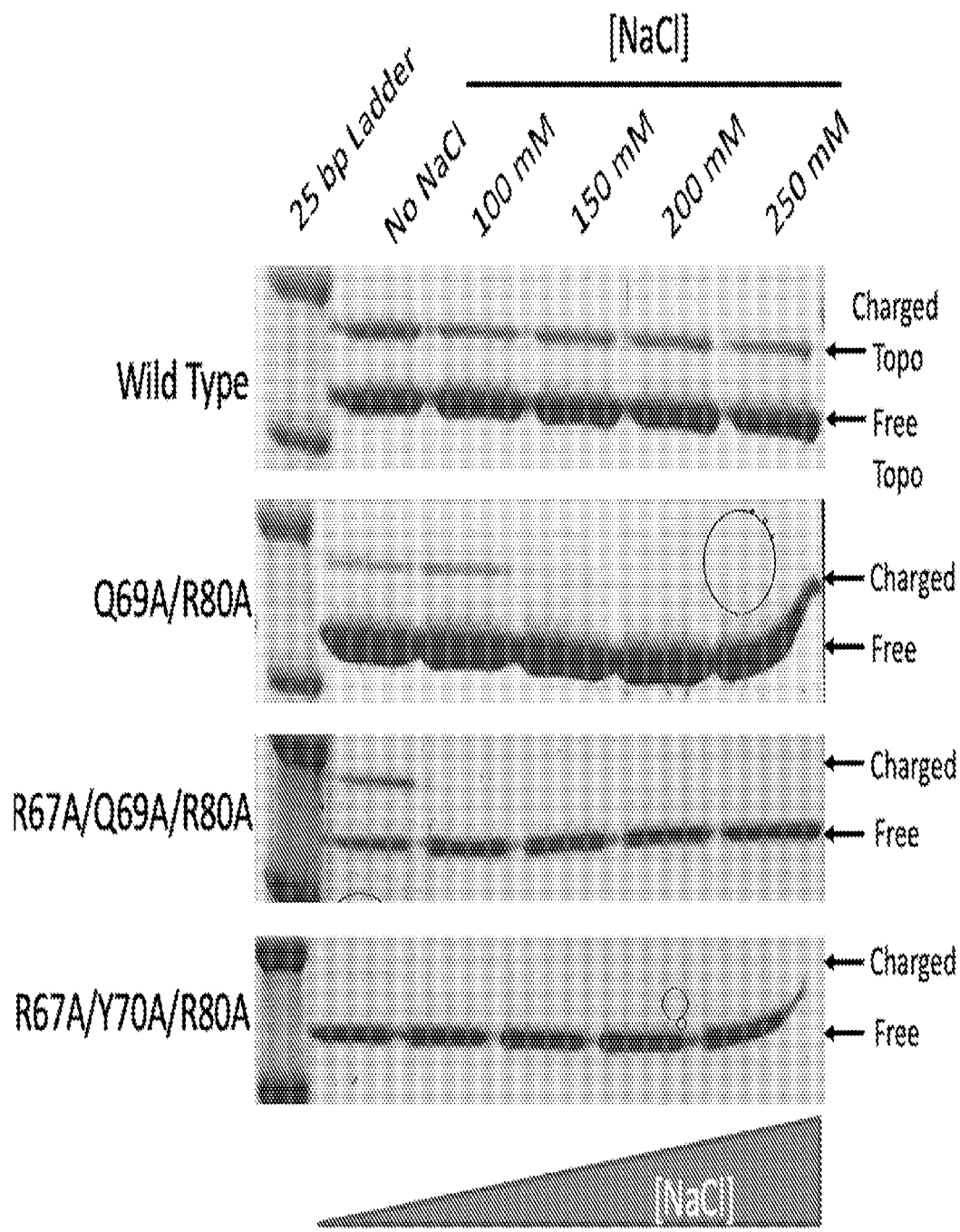
FIG. 2 depicts a SDS-PAGE gel of different topoisomerase salt sensitive mutants, showing reduced covalent binding to DNA by the salt sensitive mutants at higher salt concentrations.

FIG. 2 depicts this charging reaction with various vaccinia topoisomerases (wild type, Q69A/R80A double mutant, R67A/Q69A/R80A and R67A/Y70A/R80A triple mutants at varying concentrations of NaCl. These results demonstrate that wild type topoisomerase can charge a cassette in >250 mM NaCl, whereas the mutants are more sensitive to NaCl concentrations (69/80-150 mM NaCl; 67/69/80-<100 mM NaCl; 67/70/80-<100 mM NaCl).

Example 2—Mutant Topo's Ability To Cut DNA is Stable Over Time

Figure 3:
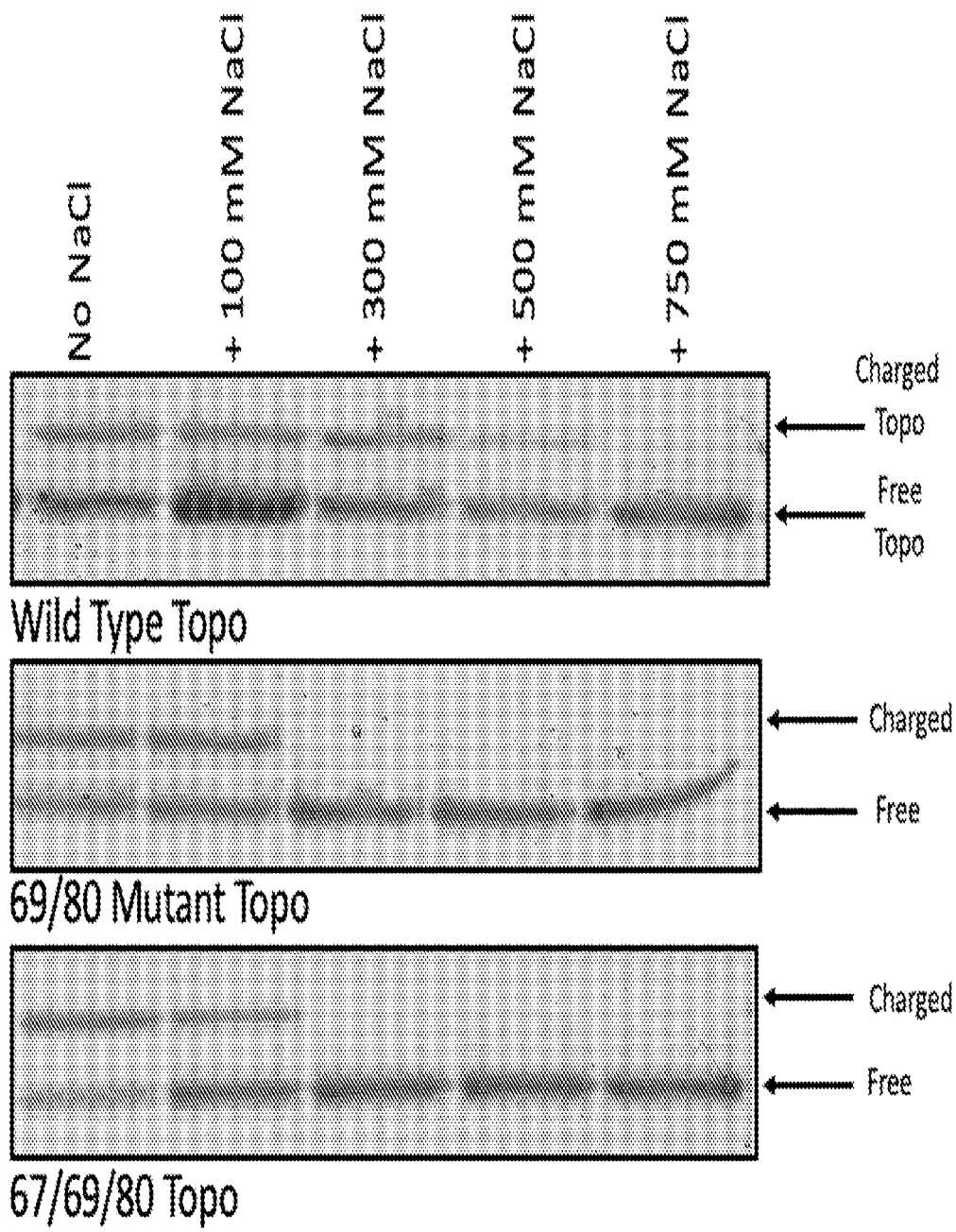
FIG. 3 depicts two-hour charging reaction with various vaccinia topoisomerase mutants, showing that the mutant's reduced ability to covalently bind to DNA is stable over time.

The charging reaction of the previous example is carried out over two hours with various vaccinia topoisomerases (wild type, 69/80 mutant and 67/69/80 triple mutant topo) at various NaCl concentrations. The results depicted in FIG. 3 show that mutant topoisomerase's ability to cleave DNA is almost identical after a two hour charging reaction compared to a fifteen minute charging reaction (shown in FIG. 2).

Example 3—Mutant Topoisomerase-Mediated DNA Ligation

Figure 4:
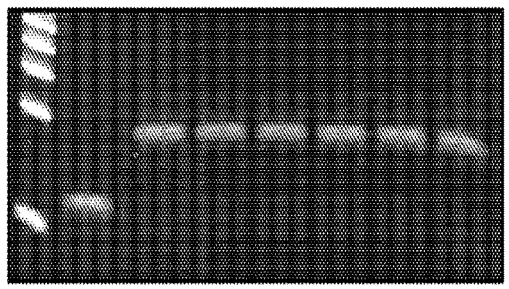
FIG. 4 depicts the ability of the mutant topoisomerase to ligate DNA under various NaCl concentrations (panel A), and a kinetic analysis of ligation (panel B).
Figure 4:
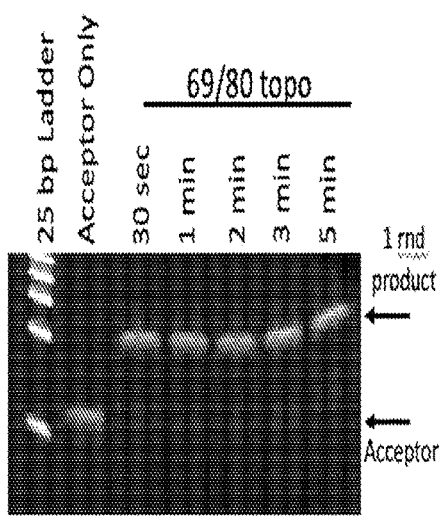

The ability and reaction kinetics of the 69/80 topoisomerase mutant to ligate DNA under various NaCl concentrations is assessed. Charged 69/80 topo is incubated with 1 pmole of the GCCG acceptor strand for fifteen minutes at 37° C. As a control, wild type topoisomerase is incubated with the GCCG acceptor in 500 mM NaCl. Results are depicted in FIG. 4, panel A. Unlike the charging reaction, which is carried out in 50 mM Tris, pH=7.4, all concentrations of NaCl tested allow for topoisomerase-mediated ligation of cassettes.

69/80 mutant topoisomerase is incubated with 1 pmole of the GCCG acceptor for various amounts of time (30 seconds-5 minutes). Samples are resolved on a 20% PAGE gel with 1×TBE buffer and stained with syber green I (Thermo-Fisher). Results are depicted in FIG. 4, panel B. The reaction is essentially at completion after 30 seconds, as no additional cassette ligation occurs after that time.

Example 4—Charging of 69/80 Topoisomerase

An optimized protocol for charging of an M-Topoisomerase of the invention, showing its feasibility for use in the methods described herein.

Invitrogen streptavidin-coated magnetic beads (20 ul, Thermo-Fisher, Cat. #65001) are washed 1×with full BW buffer (10 mM Tris, pH=8.0, 2 M NaCl, 1 mM EDTA). Washing consists of resuspending the beads to a homogenous slurry and placing against a magnet to pellet. The supernatant is then drawn off and discarded, and the beads are quickly resuspended to prevent drying out.

Beads are then washed with 0.5×BW buffer, and resuspended in 0.5×BW buffer. Biotin labelled cassette is then added to the slurry, and the beads are incubated at room temperature for 10 minutes shaking.

The bead/cassette mixture is then washed twice in 50 mM Tris, pH=7.4. After the second wash, the beads are resuspended in 50 mM Tris, pH 7.4, and 69/80 mutant topoisomerase is added. This mixture is incubated at 37° C. for 15 minutes.

The bead mixture is then placed against a magnet, and the supernatant containing the charged topoisomerase is isolated.

Five molar NaCl is added to the charged topoisomerase mixture to bring the final concentration of NaCl to 500 mM. This allows for the 69/80 mutant topoisomerase to transfer the cassette to a DNA acceptor, but at this NaCl concentration the mutant enzyme can no longer cleave DNA.

Example 5—Preparing the DNA Acceptor on S/A Beads

New England Biolabs streptavidin-coated magnetic beads (50 ul, NEB, Cat. #S14205) are washed 1×with full BW buffer (10 mM Tris, pH=8.0, 2 M NaCl, 1 mM EDTA). Washing consisted of resuspending the beads to a homogenous slurry and placing against a magnet to pellet. The supernatant is then drawn off and discarded, and the beads are quickly resuspended to prevent drying out.

Beads are then washed with 0.5×BW buffer, and resuspended in 0.5×BW buffer. Biotin labelled DNA acceptor oligonucleotide, containing an EcoRI site, is then added to the slurry, and the beads were incubated at room temperature for 10 minutes shaking.

The bead/DNA acceptor mixture is then washed twice in 50 mM Tris, pH=7.4, 500 mM NaCl. After the second wash, the beads are resuspended in 50 mM Tris, pH7.4, 500 mM NaCl. The DNA acceptor is now attached to streptavidin (S/A) beads and ready to accept DNA cassettes, mediated by charged 69/80 topoisomerase.

Example 6—Bit Addition Reaction

The wash solution containing the NEB magnetic streptavidin-coated beads bound with a biotinylated DNA acceptor oligonucleotide is removed using a magnetic to pellet the beads away from the supernatant.

Charged 69/80 mutant topoisomerase, in 500 mM NaCl is then added to the DNA acceptor, and the reaction mixture is placed at 37° C. for 15 minutes to allow for bit addition.

After a 15 minute incubation, the mixture is placed against a magnet, and the topoisomerase solution is removed.

Fifty microliters of BW solution is then added to the beads, and a homogenous slurry is formed by repeated pipetting. The solution is then allowed to incubate for 10 minutes at room temperature to remove any 69/80 mutant topoisomerase from the bead-DNA complex.

Using a magnet, the BW solution is removed and the beads are washed three times with 50 mM Tris, pH 7.4.

The beads are subsequently resuspended in 50 mM Tris containing 1U of recombinant shrimp alkaline phosphatase (rSAP, NEB, Cat. #M0371), which removes the blocking 5' phosphate on the newly added cassette. This will allow for the synthetic DNA fragment to accept another cassette. The reaction mixture is placed at 37° C. for 15 minutes to permit dephosphorylation to occur.

Following the dephosphorylation, or de-blocking step, the rSAP solution is removed and the beads are resuspended in 50 mM Tris, pH=7.4, and heated to 65° C. for twenty minutes to inactivate the phosphatase enzyme.

Following the 65° C. incubation, the beads are washed three times with 50 mM Tris, pH=7.4, 500 mM NaCl solution.

A new solution of charged 69/80 mutant topoisomerase is added to the beads-DNA acceptor complex in 500 mM NaCl, as outlined above, for a second, or subsequent round of bit addition.

The solution is then washed with BW solution as stated above, and after the final bit addition has been performed, the beads are washed three times in 1×Cutsmart buffer (NEB, Cat. #B7204, 20 mM Tris acetate, 10 mM Mg acetate, 50 mM potassium acetate, 100 µg/ml BSA, pH=7.9).

25 µl of Cutsmart buffer containing forty units of EcoRI restriction enzyme (NEB, Cat. #3101) is added to the bead-DNA acceptor complex. EcoRI will cut the DNA acceptor close the biotinylation site, thereby freeing the synthetic DNA complex comprised of the DNA acceptor and added cassettes from the streptavidin-coated magnetic bead. The mixture is incubated at 37° C. for 15 minutes.

The bead/EcoRI solution is placed next to the magnet, and the supernatant containing the synthetic DNA is removed. The reaction is resolved on a 10% or 20% PAGE TBE gel (as shown in the figures).

This bit-addition reaction can also be carried out using nanopore-based chips, e.g., as described in Method B, wherein the DNA is moved in and out of reaction chambers through a nanopore which excludes passage of the M-Topoisomerase, thus permitting controlled addition of nucleotides to build a strand having a desired sequence.

REFERENCE TO AN ELECTRONIC SEQUENCE LISTING

The contents of the electronic sequence listing (DNA-04-USD-SequenceListing.xml; Size: 19,754 bytes; and Date of Creation: Apr. 11, 2023) is herein incorporated by reference in its entirety.

The invention claimed is:

1. A topoisomerase comprising the following sequence:

SEQ ID NO: 3

RALFYKDGKLFTDNNFLNPVSDDNPAYEVLQHVKIPTHLTDVVVYEQTWE

EALTRLIFVGSDSKGX$_1$RX$_2$X$_3$FYGKMHVQNX$_4$NAKRDRIFVRVYNVMKR

INCFINKNIKKSSTDSNYQLAVFMLMETMFFIRFGKMKYLKENETVGLLT

LKNKHIEISPDEIVIKFVGKDKVSHEFVVHKSNRLYKPLLKLTDDSSPEE

FLFNKLSERKVYECIKQFGIRIKDLRTYGVNYTFLYNFWTNVKSISPLPS

PKKLIALTIKQTAEVVGHTPSISKRAYMATTILEMVKDKNFLDVVSKTTF

DEFLSIVVDHVKSSTDG wherein at least two of $X_1$, $X_2$, $X_3$, and $X_4$, are mutated from the residues in the wild type sequence [wherein in the wild-type sequence, $X_1$ is arginine (R), $X_2$ is glutamine (Q), $X_3$ is tyrosine (Y), and $X_4$ is arginine (R)] to glycine (G), alanine (A) or valine (V);

provided that where only two residues are mutated, $X_1$ and $X_2$ are not both mutated to A.

2. The topoisomerase of claim 1 wherein at least three or all of four of $X_1$, $X_2$, $X_3$, and $X_4$ are mutated to A.

3. The topoisomerase of claim 1 wherein $X_2$ and $X_4$ are A; or $X_1$, $X_2$, and $X_4$ are A; or $X_1$, $X_3$, and $X_4$ are A.

4. The topoisomerase of claim 1 which comprises one or more isolation sequences.

5. The topoisomerase of claim 1 which comprises SEQ ID NO: 4.

* * * * *